United States Patent [19]
Tseng et al.

[11] Patent Number: 4,616,802
[45] Date of Patent: Oct. 14, 1986

[54] TUBING OCCLUDER

[75] Inventors: Charles C. Tseng, Lake Bluff; Kenneth Lynn, Spring Grove, both of Ill.

[73] Assignee: Baxter Travenol Laboratories, Inc., Deerfield, Ill.

[21] Appl. No.: 678,624

[22] Filed: Dec. 6, 1984

[51] Int. Cl.⁴ .................................. F16L 55/14
[52] U.S. Cl. ................................ 251/7; 604/250
[58] Field of Search .................. 251/7, 8; 604/250

[56] References Cited
U.S. PATENT DOCUMENTS

| | | | |
|---|---|---|---|
| 2,070,143 | 2/1937 | Schisler | 251/8 |
| 3,042,067 | 7/1962 | Hidding | 251/8 |
| 3,268,201 | 8/1966 | Little | 251/8 |
| 3,554,111 | 1/1971 | Traver | 98/40 |
| 3,588,034 | 6/1971 | Powell | 251/8 |
| 3,740,017 | 6/1973 | Pogonowski | 251/5 |
| 3,791,617 | 2/1974 | Press | 251/8 |
| 4,044,989 | 8/1977 | Basel et al. | 251/7 |
| 4,071,039 | 1/1978 | Goof | 137/87 |
| 4,312,493 | 1/1982 | Stauffer | 251/8 |
| 4,316,483 | 2/1982 | Jandrasi | 251/329 |
| 4,337,791 | 7/1982 | Tech et al. | 251/8 |
| 4,429,852 | 2/1984 | Tersteegen et al. | 251/9 |
| 4,475,709 | 10/1984 | Becker, Jr. | 251/6 |
| 4,493,710 | 1/1985 | King et al. | 604/250 |

Primary Examiner—Martin P. Schwadron
Assistant Examiner—Sheri M. Novack
Attorney, Agent, or Firm—Paul C. Flattery; Daniel D. Ryan; Kay H. Pierce

[57] ABSTRACT

A flexible tubing occluding device is provided for releasably occluding flexible tubing. The tubing occluding device includes housing that is adapted to receive the tubing and defines a tubing occluding surface against which a transverse section of the tubing is transversely urged and compressed when in an occluded position. A wedge-shaped tongue member is provided for urging the transverse section of the tubing against the tubing occluding surface.

The geometry of the tubing occluding surface and the wedge-shaped tongue member cooperate to distribute a relatively low amount of force at the center portion of the occluded tubing and a relatively large force at the distal ends of the occluded tubing, utilizing the mechanical advantage of the wedge-shaped tongue member. The tubing occluding surface is configured so that the bottom half of the occluding tubing generally conforms to its original shape and so that most of the strain energy stored within the occluded tubing is utilized to allow restoration of the top half of the occluded tubing to an open position when the tubing is released from the occluded position.

10 Claims, 3 Drawing Figures

4,616,802

TUBING OCCLUDER

FIELD OF THE INVENTION

The present invention relates to a tubing occluder device and a method of occluding tubing.

BACKGROUND ART

Flexible tubing is used in numerous applications, including many medical and medical-related applications. For example, flexible tubing may be used to deliver parenteral fluids and/or medication to a patient intravenously. The flexible tubing may also be used in connection with blood dialysis, among other uses.

Often, when flexible tubing is utilized, it is necessary or desirable to prevent flow of fluid by occluding the tubing. This may be accomplished by clamping the tubing walls together so that there is essentially no open cross sectional area within the tubing. When it is desired to resume fluid flow, it is of course necessary to open the tubing.

Various types of flexible tubing which may be used include, for example, tubing constructed of flexible polyvinyl chloride, silicone polymers and other types of polymers.

Flexible tubing is usually occluded by utilizing a clamping device having two flat surfaces that advance towards each other with a transverse section of the tubing being compressed therebetween until the tubing is closed. Clamping tubing shut in this manner can result in permanent deformation of the tubing as a result of cold working and in some cases the tube remains permanently deformed and in an essentially closed position.

A need exists for a device and method which occludes flexible tubing for an extended period of time without permanently deforming or cold working the tubing.

DISCLOSURE OF THE INVENTION

In accordance with the present invention, a tubing occluder device is provided that can clamp or occlude flexible tubing for an extended period of time without causing permanent deformation or excessive cold working of the tubing that would prevent reestablishing fluid flow through the tubing. The geometry of the surfaces of the occluder utilized to occlude the tubing cause the tubing to be compressed in a configuration that utilizes strain energy, induced from the bending of the tubing, to induce tube shape restoration when the occluding device is released from the tubing.

The tubing occluding device in accordance with the present invention also minimizes the force required to occlude the tubing and decreases the stress and strain on the transverse section of the tubing that is occluded. The tubing occluder utilizes a mechanical advantage that results from the occluder geometry while minimizing cold working of the tubing.

A tubing occluding device for releasably occluding flexible tubing in accordance with the present invention includes a housing that is adapted to receive the tubing that defines a tubing occluding surface against which a transverse section of the tubing is transversely urged and compressed when in an occluded position. A wedge-shaped tongue member is provided for urging the transverse section of the tubing against the tubing occluding surface.

The tubing occluding surface of the housing includes a slightly concave mid-portion surface against which the transverse section of the tubing preferably rests when in an unoccluded position. Generally, the width or the mid-portion is equal to about one-half of the inner circumference of the tubing. At each end of the mid-portion, a sloped, planar surface is provided. Each sloped, planar surface forms an angle at the intersection with the mid-portion of between about 120° and 150° and preferably about 135°. The tubing occluding surface of the housing further includes a concave side surface that defines a pocket in the housing. The concave side surface is located at end of each sloped, planar surface opposite the end at the mid-portion of the tubing occluding surface. The transverse ends of the tubing during occlusion are adjacent part of the concave side surfaces and the sloped, planar surfaces.

The wedge-shaped tongue member defines a tongue surface for urging the tubing against the tubing occluding surface and includes a planar tongue mid-portion surface for urging the tubing against the mid-portion of the tubing occluding surface. Generally, the width of the mid-portion is equal to about one-half of the inner circumference of the tubing. The tongue surface further includes at each end of the planar tongue mid-portion surface a generally planar side portion extending from the planar tongue mid-portion that forms an angle with the intersection of the planar tongue mid-portion of between about 225° and 270° and preferably about 255° for urging the tubing against the sloped, planar surfaces and concave side surfaces of the tubing occluding surface with a mechanical advantage.

The housing and tongue are mounted for movement relative to and away from each other in a generally normal direction relative to the tubing occluding mid-portion surface and the planar tongue mid-portion for occluding and releasing the transverse section of tubing contained between said tongue and housing.

Generally, the housing will be fixed in place and the tongue portion will be movable to and away from the housing.

The housing and tongue should each have a thickness that is large enough to prevent damage to the longitudinal section of tubing that is occluded. If the housing and tongue are not sufficiently thick, the tubing could be cut or otherwise damaged. However, it is not particularly desirable to make the housing and tongue substantially thicker than the minimum thickness required to prevent damage to the tubing, since a substantially longer transverse section of tubing would be occluded requiring a greater total force to occlude the tubing.

In accordance with another aspect of the invention, a method of releasably occluding flexible tubing is provided. The method includes urging a transverse section of tubing against a tubing occluding surface with a wedge-shaped tongue surface to transversely compress the transverse section to an occluded position. The tubing occluding surface and tongue surface are as previously described.

BRIEF DESCRIPTION OF THE DRAWINGS

The present invention can be more completely understood by reference to the accompanying drawings in which.

DETAILED DESCRIPTION

Because clamping devices are well known, the present description is directed in particular to elements forming part of, or cooperating more directly with, the present invention. Structure not illustrated is understood to be well known in the art.

Figure 1:
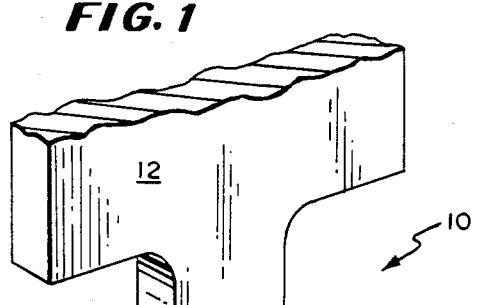
FIG. 1 illustrates a perspective front elevation view of a portion of a tubing occluder in accordance with the present invention.

Referring now to the drawings generally and in particular to FIG. 1, there is illustrated in perspective view a tubing occluder in accordance with the present invention referred to by reference numeral 10.

Tubing occluder 10 includes a movable tongue 12 and a housing 14. Tongue 12 can be manually movable or power operated.

Tongue 12 and housing 14 can be made of rigid material such as metal, plastic or similar material. Tongue 12 and housing 14 can also be made of resilient material, such as hard rubber, if desired. The surfaces of tongue 12 and housing 14 which function to occlude the tubing may comprise resilient material and the remainder of tongue 12 and housing 14 can comprise rigid material, for example.

Housing 14 is adapted to receive flexible tubing 16, as illustrated in FIG. 1. Flexible tubing 16 can be flexible polyvinyl chloride tubing, silicone polymer tubing or any other of a number of types of polymers which are used for flexible tubing.

Housing 14 defines a tubing occluding surface 18 against which a transverse section of flexible tubing 16 is urged and compressed when in an occluded position.

Tongue 12 defines a tongue surface 20 for urging tubing 16 against tubing occluding surface 18. As illustrated, the top portion of tongue 12 is cut away and would be associated with structure (not shown) for selectively moving tongue 12 towards housing 14 to an occluding position with desired force, as shown in FIG. 3, and for retracting tongue 12 from housing 14 to a position where the tubing is not compressed or occluded, such as shown in FIG. 1. The structure for selectively moving tongue 12 could comprise a solenoid or other power operated device, or manually operated structure, such as a screw clamp, for example. Structure would also be provided for maintaining tongue 12 and housing 14 in the desired relationship, such as guides 25, illustrated in FIG. 2, which are rigidly mounted to housing 14 and define slots 25a allowing movement of tongue 12 in a direction to and away from housing 14, parallel to guides 25.

Figure 2:
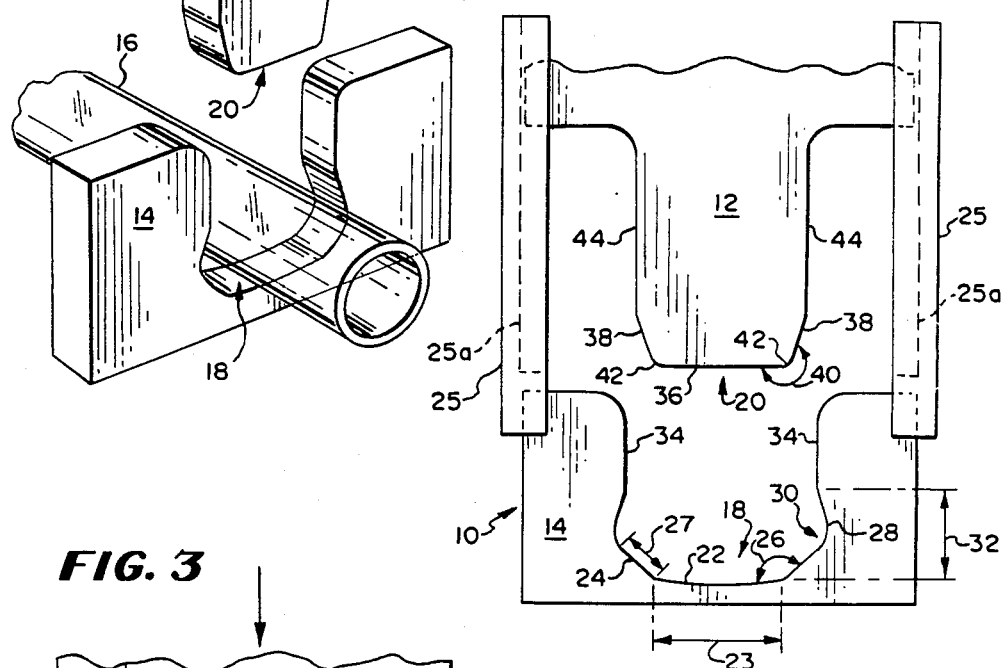
FIG. 2 illustrates an elevation view of a tubing occluder in accordance with the present invention.
Figure 3:
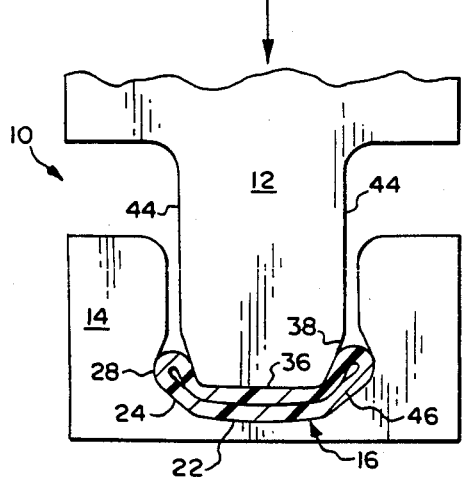
FIG. 3 illustrates an elevation view of a portion of a tubing occluder in accordance with the invention showing tubing in an occluded position.

Referring to FIG. 2, tubing occluding surface 18 and tongue surface 20 are more clearly illustrated. Tubing occluding surface 18 includes a slightly concave mid-portion 22 against which flexible tubing 16 normally rests when in an unoccluded position. Slightly concave mid-portion 22 has a width, referred to by reference numeral 23, that is about equal to one-half of the inner circumference of flexible tubing 16.

Tubing occluding surface 18 further includes at each end of slightly concave mid-portion 22 a sloped, planar surface 24 that forms an angle 26 at the intersection with concave mid-portion 22 of about 135°. The length of sloped, planar surfaces 24 referred to by reference numeral 27 is generally equal to about one-third to one-quarter of the length of concave mid-portion 22.

Preferably, and as illustrated in FIG. 2, the radius of curvature of concave mid-portion 22 is about five times the outer radius of tubing 16.

Tubing occluding surface 18 further includes a concave side surface 28 that defines a pocket 30 in housing 14 at the end of each sloped, planar surface 24 opposite the end of sloped, planar surface 24 at mid-portion 22. Preferably, and as illustrated in FIG. 2, the combined height of sloped, planar surface 24 and concave side surface 28 above mid-portion 22, referred to by reference numeral 32, is equal to about one-half of the outer diameter of tubing 16.

The side wall surfaces 34 of housing 14 can serve to define a guide for movable tongue 12 and can facilitate the containment and centering of tubing 16 but are not directly involved in the occluding of tube 16.

Tongue surface 20 of movable tongue 12 includes a planar tongue mid-portion surface 36 for urging tubing 16 against mid-portion 22 of tubing occluding surface 18. Tongue surface 20 further includes at each end of planar tongue mid-portion surface 36 a planar side portion 38 that extends from planar tongue mid-portion surface 36 and forms an angle 40 at the intersection with tongue mid-portion surface 36 of about 255°, for urging the transverse or distal ends of tubing 16 against sloped, planar surfaces 24 and concave side surfaces 28 of tubing occluding surface 18. Preferably, and as illustrated in FIG. 2, the intersection of each of planar side portions 38 and planar tongue mid-portion surface 36 defines a curved edge 42. The purpose of curved edge 42 is to uniformly distribute forces on flexible tubing 16 when in an occluded position as illustrated in FIG. 3 and to prevent deformation of tubing 16 adjacent curved edge 42 which could occur, for example, if edge 42 was not curved or rounded. The actual degree of curvature is not important as long as deformation of the tubing is prevented.

The vertical sides 44 of tongue 12 can serve to act as a guide in combination with side wall surfaces 34 of housing 14. Vertical sides 44 are not directly involved in the occluding of tubing 16.

Preferably, the length of planar side portions 38 of tongue 12 will be sufficiently long so that no portion of vertical sides 44 contact tubing 16.

FIG. 3 illustrates tubing occluder 10 in an occluded position and illustrates the cross section of flexible tubing 16 that has been occluded.

In FIG. 3, tongue 12 has been advanced upon tubing 16 with sufficient downward force to occlude tubing 16. The central portion of tubing 16, which is adjacent concave mid-portion 22 and planar tongue mid-portion 36 is relatively easy to occlude, requiring a relatively low force. The concave curvature of concave mid-portion 22 reduces the force on the center of the tube and also reduces the wear rate of the tubing. The peripheral portions 46 of occluded tubing 16 are each bent upwardly and are in the form of a teardrop shape. Planar side portions 38 of tongue surface 20 urge peripheral portions 46 of tubing 16 against sloped planar surfaces 24 and concave side surfaces 28 with a mechanical advantage because of the angle form between tongue mid-portion surface 36 and planar side portions 38. As a result, more force is directed to peripheral portions 46 of tubing 16 which are the sections of tubing 16 that are the most difficult to occlude. The combination of sloped, planer surfaces 24 and concave side surfaces 28 provide sufficient space from planar side portions 38 so that peripheral portions 46 are not crimped.

The bottom of occluded tubing 16 in FIG. 3, which includes those portions of the wall of tubing 16 in contact with concave mid-portion 22, sloped, planar surfaces 24 and concave side surfaces 28, conforms generally to the original shape of that portion of tubing 16. Peripheral portions 46 of tubing 16 contain most of the strain energy stored within occluded tubing 16. Since the bottom half of tubing 16 conforms generally to its original shape, when tongue 12 is retracted, most of the strain energy stored within occluded tubing 16 is utilized to cause the top half portion of occluded tubing 16 to spring back.

In the illustrated embodiment, tubing occluder 10 avoids the use of sharp edges, which tend to permanently deform flexible tubing. In addition, the design of tubing occluder 10 provides a desired distribution of forces to occlude the tubing. The design transmits a relatively low force at the center portion of the occluded tubing and provides a relatively greater force at the distal portions of the tubing through the use of a mechanical advantage that is derived from the wedge shape of the movable tongue. The resulting effect is that the force required to occlude tubing is minimized. Since the forces exerting upon tubing are minimized, the life of the tubing is increased.

As illustrated in FIG. 3, the cross-sectional area of the tubing wall remains constant. However, the tubing walls become thinner which results in the expansion of the inner and outer circumference of tubing 16. This is due to a plane strain phenomenon.

While the invention has been described with respect to preferred embodiments, it will be understood that the invention is capable of numerous changes, modifications and rearrangements and such are intended to be covered by the appended claims.

We claim:

1. A device for releasably occluding a flexible tubing comprising:
   a housing adapter to receive said flexible tubing and defining a recessed tubing occluding surface against which a transverse section of the tubing is transversely urged and compressed when in an occluded position;
   a wedge-shaped tongue for urging the transverse section of the tubing against said tubing occluding surface;
   said tubing occluding surface including a slightly concave mid-portion, said slightly concave mid-portion extending transversely to said tubing when said tubing is received in said housing, said tubing occluding surface further having at each transverse end of said concave mid-portion a sloped, planar surface, each sloped, planar surface forming an angle at the intersection with said concave mid-portion of between about 120° and 150°, a concave side surface defining a pocket in said housing at the end of each sloped, planar surface opposite the end of each sloped, planar surface at said mid-portion;
   said tongue defining a tongue surface for urging said transverse section of tubing against said tubing occluding surface and including a planar tongue mid-portion surface generally parallel to and substantially corresponding in width to said slightly concave mid-portion of said tubing occluding surface for urging said transverse section of tubing against said mid-portion of said tubing occluding surface, and tongue surface further including at each transverse end of said planar tongue mid-portion surface a planar side portion extending from said planar tongue mid-portion and forming an angle with the intersection of said planar tongue mid-portion of between about 225° and 270° for urging transverse ends of the tubing against said sloped planar surfaces and concave side surfaces of said tubing occluding surface;
   said housing and tongue being mounted for movement relative to and away from each other in a generally normal direction relative to said tubing occluding mid-portion surface and said planar tongue mid-portion surface for occluding and releasing the transverse section of tubing contained between said tongue and housing.

2. The device of claim 1 wherein the width of said concave mid-portion is equal to about one-half of the inner circumference of the tubing.

3. The device of claim 1 wherein said housing is fixed and said tongue is movable to and away from said housing.

4. The device of claim 1 wherein the angle formed at the intersection of each of said planar surfaces with said concave mid-portion is about 135°.

5. The device of claim 1 wherein each concave side surface comprises a curved indentation having a radius of curvature of about one-third of the outer radius of the tubing.

6. The device of claim 1 wherein the intersection of each of said planar side portions and said planar mid-portions of said tongue defines a curved edge.

7. The device of claim 1 wherein said housing and tongue each have a thickness sufficient to prevent damage to the tubing.

8. The device of claim 1 wherein the intersection of said tongue planar mid-portion and said tongue side portions each form an angle of about 255°.

9. The device of claim 1 wherein said slightly concave mid-portion has a radius of curvature that is about five times the outer radius of the tubing.

10. The device of claim 1 wherein the surfaces of said housing and tongue comprise resilient material.

* * * * *